No. 12,384 REISSUED AUG. 29, 1905.

E. F. BILLINGS.

APPARATUS FOR GENERATING FORMALDEHYDE.

APPLICATION FILED JUNE 24, 1905.

Witnesses:
H. L. Robbins
A. C. Ratigan

Inventor:
E. F. Billings
by Wright, Brown, Quinby and Gray,
Attorneys.

UNITED STATES PATENT OFFICE.

EDGAR F. BILLINGS, OF BOSTON, MASSACHUSETTS.

APPARATUS FOR GENERATING FORMALDEHYDE.

No. 12,384. Specification of Reissued Letters Patent. Reissued Aug. 29, 1905.

Original No. 732,159, dated June 30, 1903. Application for reissue filed June 24, 1905. Serial No. 266,898.

*To all whom it may concern:*

Be it known that I, EDGAR F. BILLINGS, of Boston, in the county of Suffolk and State of Massachusetts, have invented certain new and useful Improvements in Apparatus for Generating Formaldehyde, of which the following is a specification.

This invention has for its object to provide as an article of manufacture and commerce a formaldehyde-vapor generator having the characteristics of a cartridge, in that it is charged and ready for use when placed upon the market and can be used by the purchaser by igniting one of the constituent parts of the cartridge, the heat thus produced causing the vaporization of another constituent part, the body or holding portion of the cartridge being of relatively inexpensive construction and adapted to be discarded after use.

The invention consists in the improved apparatus or cartridge, which I will now proceed to describe and claim.

Figure 1:
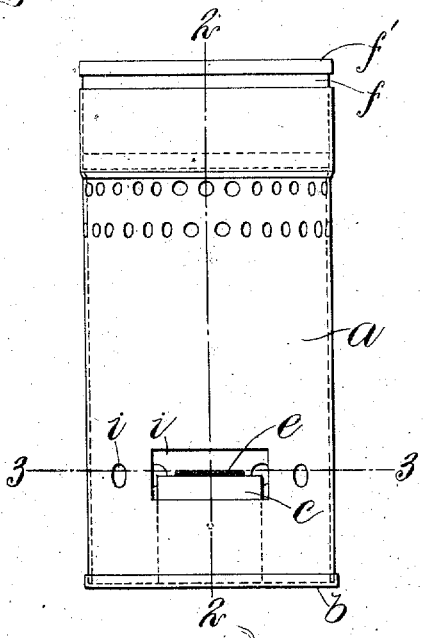
Figure 3:
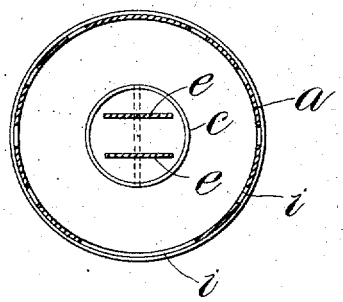
Figure 4:
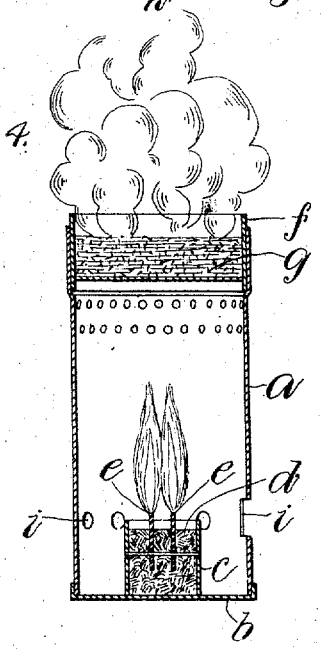
Figure 2:
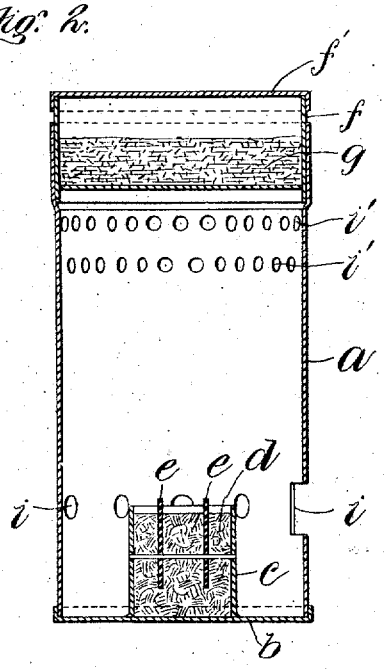

Of the accompanying drawings, forming a part of this specification, Figure 1 represents a side elevation of a vaporizing apparatus embodying my invention. Fig. 2 represents a section on line 2 2 of Fig. 1. Fig. 3 represents a section on line 3 3 of Fig. 1. Fig. 4 represents a view similar to Fig. 2, but on a smaller scale, showing the apparatus in operation.

The same reference characters indicate the same parts in all the figures.

In the drawings, *a* represents a tubular casing, preferably of non-combustible material, such as sheet metal, said casing having a bottom piece *b*, to which is affixed a socket *c*, containing a mass *d* of combustible material, which may be solidified hydrocarbon, such as paraffin or spermaceti, and a wick or wicks *e*, embedded in the said mass, the said mass *d* and wick *e* constituting a combustible charge which when ignited generates heat for vaporizing purposes, as hereinafter described.

*f* represents a box or reservoir which is preferably detachably fitted to the upper end of the casing *a* and constitutes a cover for said casing, the bottom of the reservoir *f* constituting a crown-sheet which is exposed to the heat generated in the combustion-chamber formed by the portion of the casing below the reservoir *f*. The reservoir *f* contains a charge *g*, which may be the ordinary solution of formaldehyde, or it may be polymerized formaldehyde, and said charge is protected and retained in place prior to the use of the apparatus by a cover *f'*, which tightly and detachably fits the reservoir *f*.

When the combustible charge *d e* is ignited, the heat generated in the combustion-chamber impinging against the crown-sheet formed by the bottom of the reservoir *f* causes the charge *e* to give off formaldehyde-vapor, and the said vapor is permitted to escape by the removal of the cover *f'*.

I prefer to proportion the charges of vaporizable and combustible material, so that they will be consumed simultaneously. Thus when the apparatus has been once used nothing will remain but the non-combustible portions, these being of relatively inexpensive construction, so that they can be discarded.

It will be seen that the device above described constitutes an article of manufacture which can be readily kept in stock by dealers and can be conveniently used by consumers, the apparatus or cartridge being put in operation by simply igniting the wick or wicks *e* and removing the cover *f'*.

I prefer to provide the lower portion of the casing *a* with orifices *i* for the admission of air to support the combustion, one of said orifices being preferably elongated to permit the insertion of a lighted match to ignite the wicks *e*. The upper portion of the casing is preferably provided with smaller orifices *i'* for the escape of the products of combustion.

I claim—

A vaporizing apparatus comprising, first, a casing having at one end a bottom piece, and a socket secured thereto and containing a combustible charge consisting of a body of combustible material, the casing constituting a combustion-chamber above said charge; and secondly, a reservoir constituting a crown-sheet for said combustion-chamber and containing a charge of vaporizable material which when heated gives off formaldehyde-vapor, said reservoir having a cover which protects the vaporizable charge prior to vaporization and is removable to permit the escape of the vapor, the whole constituting a vaporizing-cartridge adapted to be marketed as an article of manufacture and discarded after the consumption of the charges.

In testimony whereof I have affixed my signature in presence of two witnesses.

EDGAR F. BILLINGS.

Witnesses:
C. F. BROWN,
E. BATCHELDER.